(12) United States Patent
Pedrazzini

(10) Patent No.: US 9,248,980 B2
(45) Date of Patent: Feb. 2, 2016

(54) PROCESS STATION OF DEVICES FOR CONVEYING BIOLOGICAL PRODUCT CONTAINERS

(71) Applicant: Inpeco Holding Ltd., Qormi (MT)

(72) Inventor: Gianandrea Pedrazzini, Paradiso (CH)

(73) Assignee: INPECO HOLDING LTD., Qormi (MT)

( * ) Notice: Subject to any disclaimer, the term of this patent is extended or adjusted under 35 U.S.C. 154(b) by 0 days.

(21) Appl. No.: 14/358,812

(22) PCT Filed: Nov. 13, 2012

(86) PCT No.: PCT/EP2012/072518
§ 371 (c)(1),
(2) Date: May 16, 2014

(87) PCT Pub. No.: WO2013/072318
PCT Pub. Date: May 23, 2013

(65) Prior Publication Data
US 2014/0346009 A1    Nov. 27, 2014

(30) Foreign Application Priority Data

Nov. 16, 2011    (IT) .............................. MI2011A2082

(51) Int. Cl.
| | |
|---|---|
| B65G 29/00 | (2006.01) |
| G01N 35/04 | (2006.01) |
| B65G 47/244 | (2006.01) |
| B65G 47/46 | (2006.01) |

(52) U.S. Cl.
CPC ................ *B65G 47/46* (2013.01); *G01N 35/04* (2013.01)

(58) Field of Classification Search
CPC .............. G01N 2035/0467; G01N 2035/0468; B65G 47/244
USPC ........ 198/347.4, 364, 464.1, 474.1, 597, 598, 198/617, 890; 436/47, 48
See application file for complete search history.

(56) References Cited

U.S. PATENT DOCUMENTS

| | | | |
|---|---|---|---|
| 4,750,620 A * | 6/1988 | Braschos | 209/523 |
| 5,941,366 A | 8/1999 | Quinlan et al. | |
| 5,966,309 A * | 10/1999 | O'Bryan et al. | 700/225 |
| 6,056,106 A * | 5/2000 | van Dyke et al. | 198/346.1 |
| 6,240,335 B1 * | 5/2001 | Wehrung et al. | 700/230 |
| 6,343,690 B1 * | 2/2002 | Britton et al. | 198/867.06 |
| 6,413,780 B1 * | 7/2002 | Bach et al. | 436/48 |
| 6,458,324 B1 * | 10/2002 | Schinzel | 422/65 |
| 6,498,037 B1 * | 12/2002 | Carey et al. | 436/50 |

(Continued)

FOREIGN PATENT DOCUMENTS

| | | |
|---|---|---|
| EP | 2 225 567 | 9/2010 |
| WO | 2008/043394 A1 | 4/2008 |
| WO | 2009/068555 A1 | 6/2009 |

*Primary Examiner* — Douglas Hess
(74) *Attorney, Agent, or Firm* — Jacobson Holman, PLLC.

(57) ABSTRACT

There is described a process station of devices for conveying biological product containers comprising a main lane for the flow of said conveying devices and a secondary lane for the flow of said conveying devices connected to each other by connection stretches. Said process station comprises a diverting unit of said conveying devices from said main lane to said secondary lane and a return unit of said conveying devices from said secondary lane to said main lane, said diverting and return unit being provided with means adapted to allow the continuous flow without stop of said conveying devices between said main lane and said secondary lane.

8 Claims, 14 Drawing Sheets

(56) References Cited

U.S. PATENT DOCUMENTS

| | | | |
|---|---|---|---|
| 6,520,313 B1* | 2/2003 | Kaarakainen et al. | 198/369.5 |
| 7,124,876 B2* | 10/2006 | Wolf | 198/370.08 |
| 7,858,032 B2* | 12/2010 | Le Comte et al. | 422/65 |
| 7,939,020 B2* | 5/2011 | Nogawa et al. | 422/65 |
| 8,037,993 B2* | 10/2011 | Pedrazzini | 198/394 |
| 8,232,103 B2* | 7/2012 | Miller et al. | 436/47 |
| 8,757,352 B1* | 6/2014 | Daboub et al. | 198/367 |
| 8,877,128 B2* | 11/2014 | Fukugaki et al. | 422/65 |
| 8,894,930 B2* | 11/2014 | Mizumoto | 422/67 |
| 8,926,902 B2* | 1/2015 | Pedrazzini | 422/65 |
| 2008/0318306 A1 | 12/2008 | Le Comte et al. | |
| 2010/0300831 A1 | 12/2010 | Pedrazzini | |

* cited by examiner

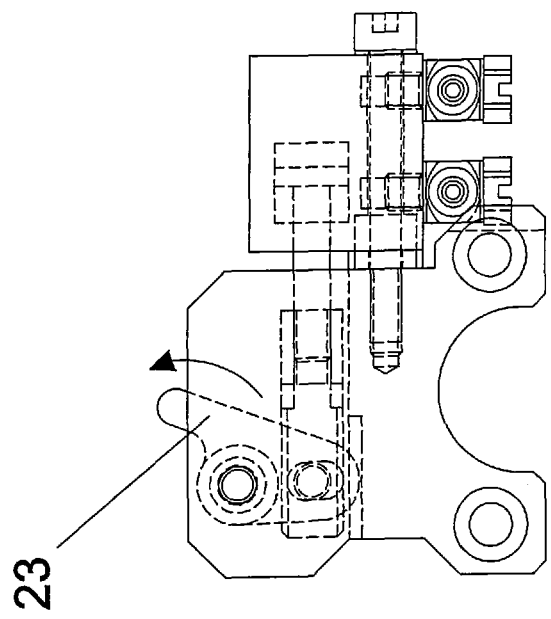
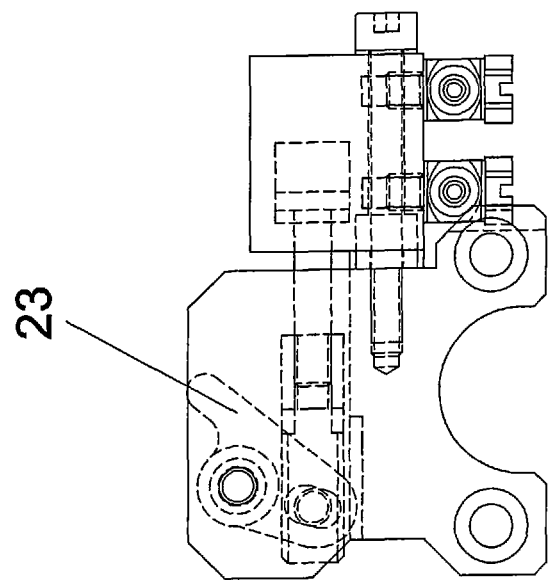
Fig.9

PROCESS STATION OF DEVICES FOR CONVEYING BIOLOGICAL PRODUCT CONTAINERS

The present invention relates to a process station of devices for conveying biological product containers.

Nowadays, in laboratories for testing biological material specimens, the use of automated systems that ensure the automatic identification, conveying and addressing of these specimens towards different points of the laboratory is increasing. In particular, the Applicant has already filed the prior patent EP-2225567 which describes a system of this type.

The system described comprises an automatic conveyor in which the biological product containers travel each inside a conveying device (also referred to as "carrier") on conveyor belts along lanes for being suitably addressed to the various modules that interface with such an automation system, whether they are actual testing modules or designed each to carry out a specific pre- or post-testing operation on the containers upon their arrival (for example loading/unloading, uncapping, recapping, content centrifugation and so on).

The automatic conveyor consists of single process stations positioned in series one after the other and all comprising a main and a secondary lane. In particular, through the management by a control unit, the intelligent automation system of the laboratory is capable of sorting every single conveying device and the relevant container within each of said process stations based on the type of operations to be carried out thereon, and this corresponds to the diversion or not of the conveying device from the main transit lane to the secondary lane, as well as the subsequent return of the previously diverted conveying device to the main lane.

In order to track its path and control its correct addressing within every single process station, the position of the moving conveying device is recorded by an apparatus for detecting conveying devices. Such an apparatus is capable of identifying the presence and identity of the conveying device in real time over the path thereof along the conveying system. It is based on a Radio Frequency identification (RFID) technology consisting of a network of antennas distributed underneath the conveyor belt of the conveying system which, upon the passage of the conveying device, are capable of receiving the data transmitted by a transponder contained in the body of the conveying device.

Such a transponder is a device provided with internal memory capable of storing and transmitting data; it does not require power supply since it is powered by the magnetic field generated by the network of antennas. Upon the passage of the conveying device on the belt close to an antenna, the electromagnetic field generated by the antenna powers the transponder which, modulating such an electromagnetic field, transmits the data stored on its memory to this antenna. What is stored on the memory of a conveying device transponder is an identification code that allows the conveying device itself to be recognized. It is unique, that means that each conveying device is associated with a unique and personal identification code. Once received by the antenna, the identification code information is sent to the control unit which, based on the location of the antenna that has sent the information, associates the location of the conveying device on the belt. The antennas located underneath the belt are strategically distributed along the conveying system: an antenna is provided at each point where it is necessary to control or know the identity of a conveying device for deciding the path thereof and storing the lifecycle thereof (for example, at the diversion points between main and secondary lane or at the points where the biological product containers are processed by the modules).

The identification of a conveying device by an antenna is allowed by the presence of a stopping gate located close to each antenna. The stopping gate blocks the conveying device right at the point where the antenna is located, underneath the belt, allowing the antenna to receive the identification code thereof sent by the transponder of the conveying device. The ID information of the conveying device identified by the antenna is communicated to the control unit, which optionally addresses the conveying device towards the suitable pre-testing, testing or post-testing modules diverting the path thereof from the main lane to the secondary lane by the projection of a pneumatically actuated lever from the inner side wall of the main lane.

Likewise, whenever a conveying device, after having interfaced with a predetermined operating module, is released since the processing thereon has ended and it must be returned to the main lane, the passage of the conveying devices along the main lane must be blocked at the same time to prevent the returning conveying device from crashing into one of the latter, causing a block in the flow of the conveying devices along the automation. In known solutions, the object is achieved by a sensor that detects the passage of the conveying device, typically in the final stretch of the secondary lane, to then communicate with the control unit which blocks, again by means of a stopping gate, any passage of a conveying device coming from the main lane thereof.

Therefore, problems occur both as regards the diversion of the conveying devices and their subsequent return, due to the fact that in known solutions the two processes are slowed down.

In fact, in the first case, it is always necessary to stop every conveying device by means of a stopping gate, as just described, close to the diversion itself to allow the antenna located underneath the belt to read the ID of the conveying device and suitably address it, either diverting it or not, after interacting with the control unit.

In the second case, whenever a conveying device must return from the secondary lane to the main lane, the above mechanism must be actuated to block the passage of the conveying devices along the main lane.

In general, the flow of conveying devices along the process station is therefore slowed down at both steps of diverting the conveying devices on the secondary lane (so that they interface with a predetermined operating module) and subsequently returning to the main lane. Considering that a laboratory automation system consists of a plurality of process stations, each of which carries out a specific operation on the specimens, it is understood that specimen after specimen, and station after station, the resulting slowing down is clear.

Moreover, any errors or malfunctions in the actuation of the gate in both steps may cause the failed stop of the conveying devices coming from the main lane. In the case of diversion, therefore, the antenna located close to the gate fails to identify the conveying device, and this may lead to an error in addressing conveying devices that should be diverted and instead continue along the main lane or vice versa, especially when several conveying devices arrive at the diversion point in a sequence. Likewise, in the case of return, a collision with the conveying device returning from the secondary lane and thus a block in the flow of conveying devices become unavoidable.

This is certainly not admissible in a system for conveying biological specimens that is assumed to be fully automated and capable of working at night time too, without needing the supervision of any technician.

U.S. Pat. No. 5,941,366 describes a multiple lane tube container conveying system with means adapted to divert said containers from one lane to the other.

The object of the present invention is to speed up both the step of reading and subsequently addressing every single conveying device along the suitable lane, and that of returning the conveying devices, previously diverted, from the secondary lane to the main lane, thus considerably increasing the flowing frequency thereof within every single process station and, by extension, along the whole automation system.

All of this must be achieved without causing any waiting queues or blocks in the flow of the conveying devices.

Another object is to ensure an error-free addressing in the diversion step even if a considerable number of conveying devices in a queue arrive close to the diversion point.

A further object is to prevent potential collisions between the returning conveying devices and those traveling on the main lane.

These and other objects are achieved by a process station of devices for conveying biological product containers as described in claim 1.

These and other features of the present invention will become more apparent from the following detailed description of an embodiment thereof, provided by way of a non-limiting example with reference to the accompanying drawings, in which:

FIG. 9 shows a detail of the detail shown in FIG. 8 in two different operative steps;

Figure 1:
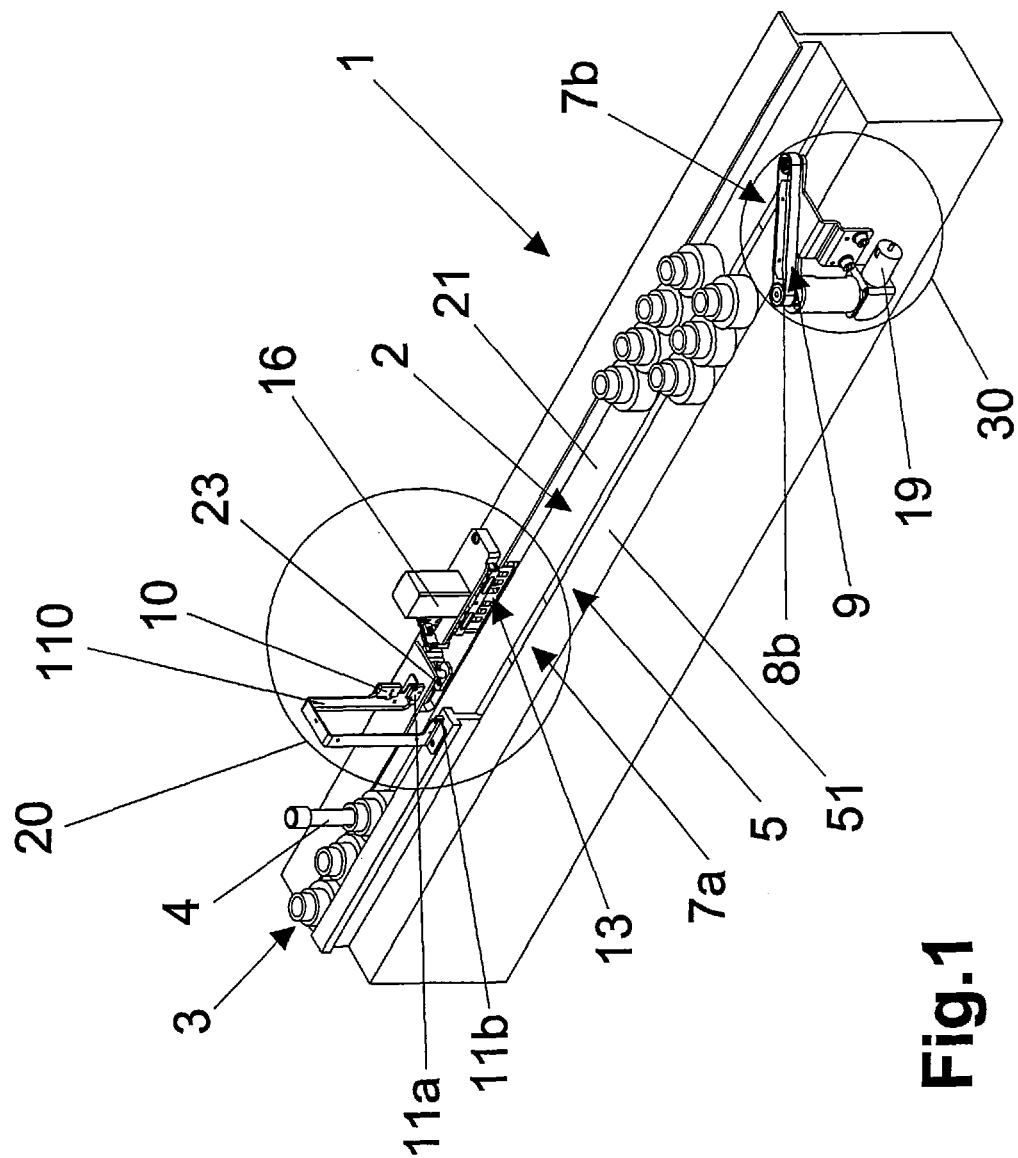
FIG. 1 shows a perspective view of a general process station belonging to an automatic conveyor of a laboratory automation system, with the control unit having been removed.

A system for the automatic identification, conveying and addressing of biological material specimens ("automation system") consists of a series of process stations 1, as shown in FIG. 1, assembled together in a variable number and according to different configurations to meet the different requirements of the testing laboratories that use the present invention.

The system, and accordingly every single station 1, comprises main conveying lanes 2 serving the function of:
conveying devices 3 (i.e. devices adapted to convey biological product containers, as described in the international patent application WO-2008043394 to the Applicant) containing these biological product containers 4, for example tubes, or empty conveying devices to be filled with tubes;
addressing said conveying devices 3 as needed towards secondary conveying lanes 5, parallel to the main lanes 2 and located externally with respect to them, which allow these conveying devices 3 to reach pre-testing, testing (or analyzers, instruments adapted to carry out tests on biological material specimens) or post-testing modules or stations, located next to the secondary lane. However, since these modules are not an object of the present invention, they will not be described but only quoted in order to provide a clearer explanation of the conveying system.

The reciprocally parallel main 2 and secondary lanes 5 accommodate horizontally-placed motorized conveyor belts 21, 51 serving the function of conveying the conveying devices 3. Each module has a pair of belts 21, 51 running in one direction and a pair of belts 21, 51 running in the opposite direction, with the function of a pair of outward lanes and a pair of return lanes. The figures show only one of these two pairs of belts 21, 51.

For the structural details of every single process station and thus by extension of the whole system, reference should be made to the description provided in patent EP-2225567 to the Applicant.

Connection stretches 7a and 7b are provided between secondary and main lanes 5, 2 which may not be regarded as actual lanes even though they substantially are, and they represent the points at which the conveying devices 3 move from the main lane 2 to the secondary lane 5 or vice versa, according to the methods that will be better explained hereinafter.

Figure 2:
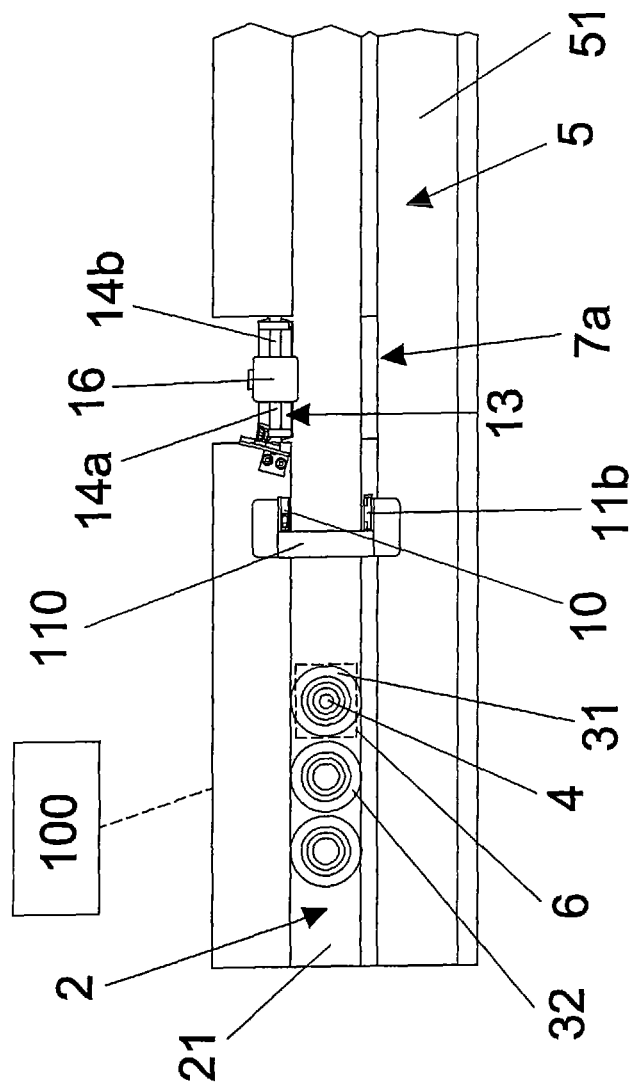
FIGS. 2-7 show a top view of various operative steps of the diverting unit.

A diverting unit 20 is provided which, in a position underneath the motorized conveyor belts 21, 51 and located upstream of the connection stretch 7a, comprises identification and control means 6 of the conveying devices (FIG. 2). They are advantageously based on an RFID technology and comprise an antenna capable of detecting the passage of each conveying device 3 through the communication with a transponder contained inside the conveying device 3 itself.

Antenna 6 is in turn electrically connected to two detection sensors mounted laterally with respect to the main lane 2: in particular, they are a tube detection sensor 10 and a conveying device detection sensor consisting of an emitter 11a and a receiver 11b. The tube detection sensor 10 is aligned with emitter 11a, i.e. located thereon.

Figure 10:
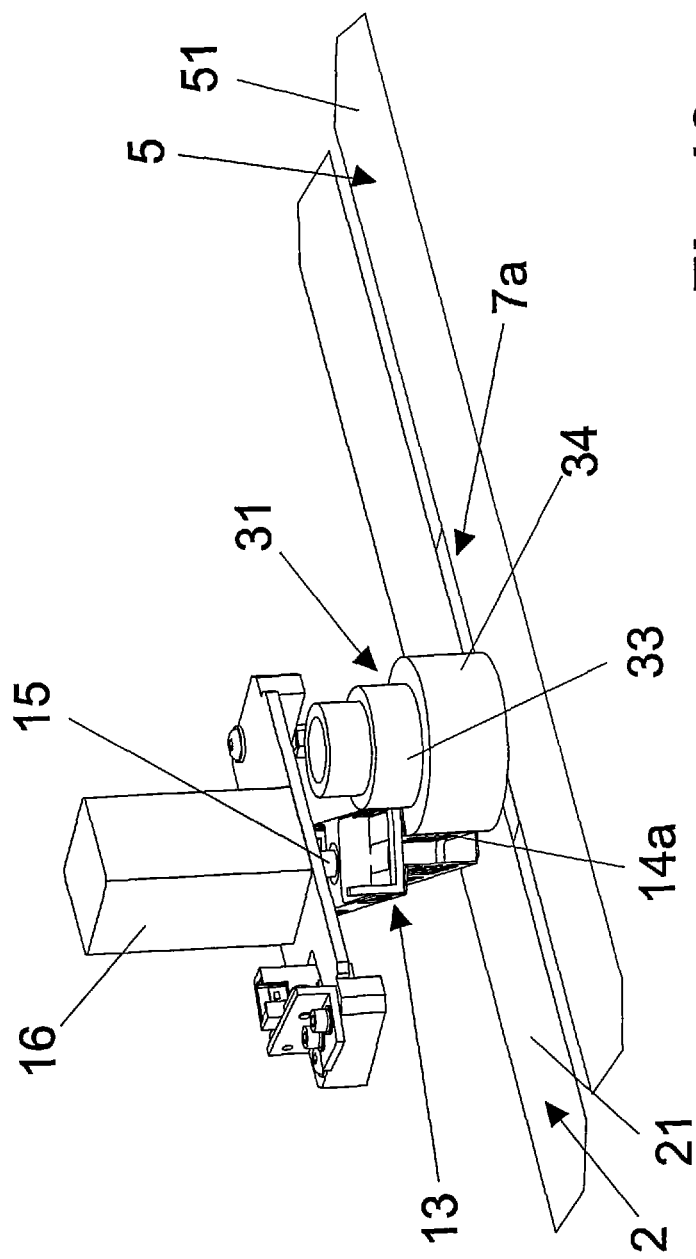
FIG. 10 shows in detail an operative step of a part of the diverting unit engaged with a conveying device.

The sensor consisting of the two parts 11a and 11b, facing each other on the opposite sides of the main lane 2 and electrically connected to each other by a bridge 110, is in turn synchronized with a diverting device 13, advantageously a cam rotating around a central shaft 15 of an electrical motor 16 (FIG. 10). Cam 13 is provided with a shaped profile that allows it to concurrently impact collar 33 and body 34 of the conveying device 3, as it will be better explained hereinafter.

Figure 8:
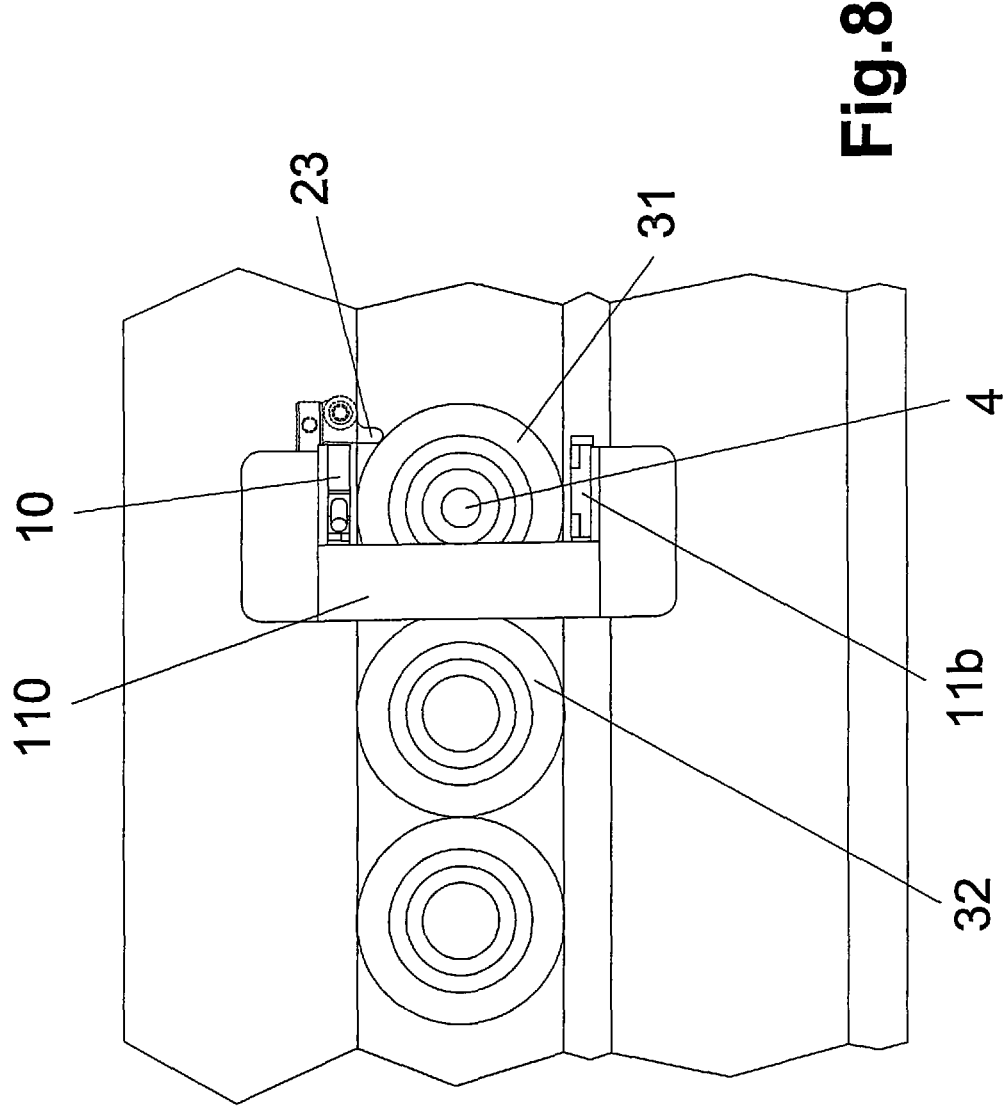
FIG. 8 shows, again in a top view, a detail of the diverting unit, in an emergency situation in which the conveying devices are blocked.

On the side of the main lane 2, preferably along the same side on which sensor 10 and emitter 11a are provided, a stopping gate 23 can come out in special emergency conditions which blocks the flow of the conveying devices 3 (FIGS. 8 and 9).

Moreover, there is provided a control unit 100 for the whole automation system, depicted for convenience in connection with only the process station 1 (FIG. 2), and capable of communicating with the process station 1 thus overriding the plurality of operations the devices belonging to the station 1 itself are involved into.

The control unit 100 may be application software installed on a personal computer, provided with memory containing all the information required to carry out the correct activities on tubes 4 and adapted to store the lifecycle thereof during the process. The information related to the tube includes for example the personal information of the individual from whom the biological material has been collected, the tests to be carried out on such a biological material and in some cases, the urgency level at which the tube must be processed.

The control unit 100 therefore manages the suitable addressing of the conveying devices 3 containing tubes 4 along the process station 1 and by extension, along the whole automation system; of course, it equally manages the addressing of empty conveying devices 3 not containing tubes. To this end, in FIGS. 2-7, by way of an example, the first one of the conveying devices 31 in queue close to the diverting unit 20 contains a tube 4 while the other ones are empty.

All the devices mounted on the system are connected to the control unit 100 so as to communicate therewith receiving commands in real time.

Figure 13:
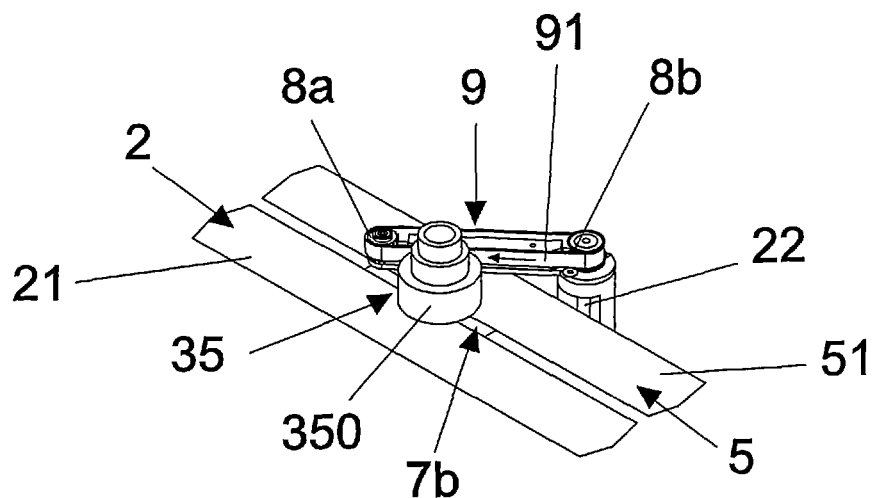
FIG. 13 shows a detail of the return unit and of a conveying device engaged therewith.

On the other hand, as regards the return unit 30, on the outer side of the connection stretch 7b it comprises a vertically-placed, preferably elastic belt 9 engaged with two pinions 8a and 8b with vertical axis of rotation (FIG. 13). A shaft 22 with vertical axis of rotation, set in rotation by an electrical motor 19, transmits the rotating movement thereof to pinion 8b, which in turn actuates belt 9.

Figure 11:
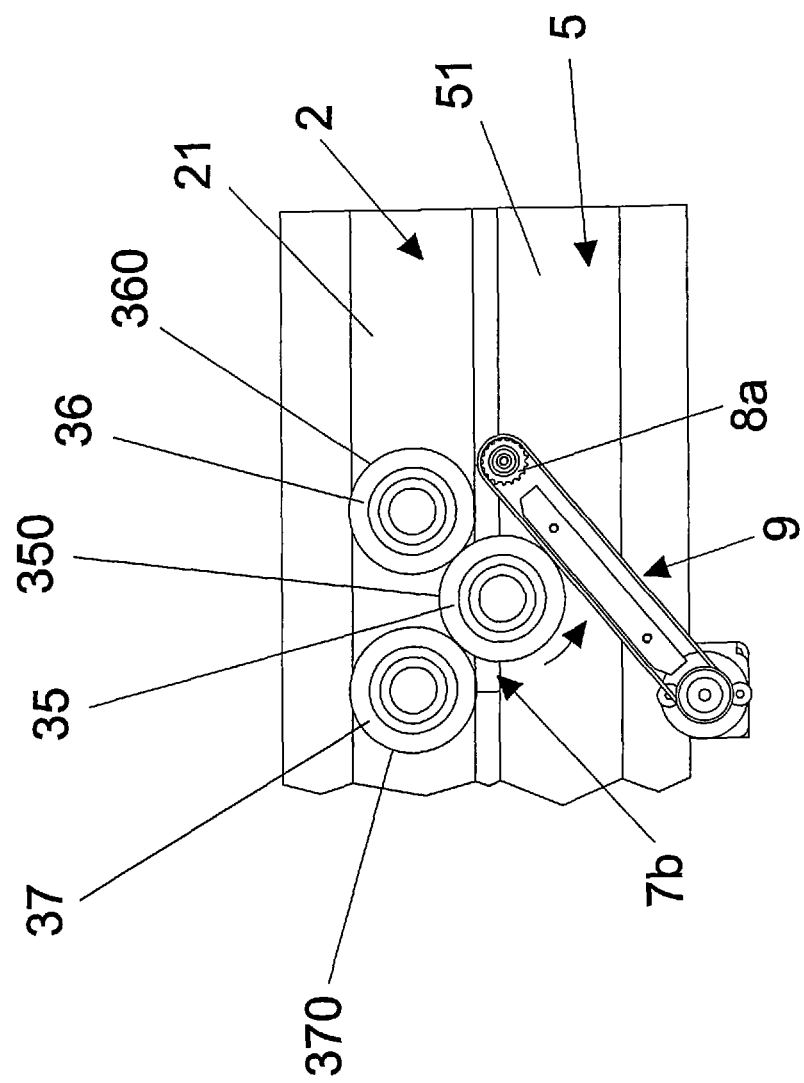
FIG. 11 shows a top view of a first operative step of the return unit, with a conveying device coming from the secondary lane in the step of introduction into the connection stretch.
Figure 12:
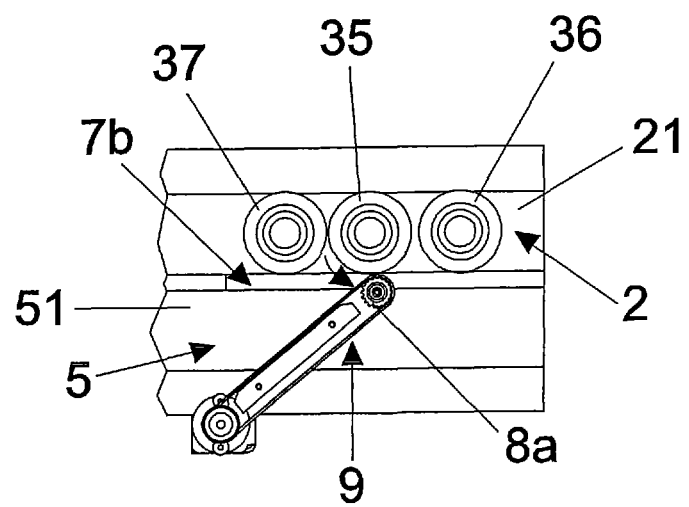
FIG. 12 shows, again in a top view, a detail of the step in which the conveying device returns from the secondary lane to the main one.

Three different conveying devices 35, 36 and 37 are listed in FIGS. 11 and 12 to better illustrate the flow of these conveying devices along the return unit 30, as it will become more apparent hereinafter.

The conveying device 35 comprises an outer side cylindrical surface 350 adapted to interact with belt 9, more in detail, the vertically-placed flat supporting surface 91 (FIG. 13).

The operation is as follows: a plurality of conveying devices 3, containing or not containing tubes 4 and coming from prior process stations connected upstream of station 1, travel on the conveyor bell 21 in the stretch of main lane 2 before the connection stretch 7a. The illustrated embodiment (FIGS. 2-7) shows a series of conveying devices 3 traveling substantially close, one after the other, in the subject stretch of main lane 2. For convenience, the first two ones of these conveying devices have been numbered with reference numerals 31 and 32.

For every single conveying device, once arrived at the conveyor belt portion with antenna 6 (FIG. 2) thereunder, the unique ID of the conveying device itself is detected by the antenna 6 itself, through the communication with the transponder contained in the conveying device, and the position of the conveying device along the process station 1 at that exact moment is thus associated therewith. In FIG. 2, this is shown with reference to the first conveying device 31 in the series.

Since the control unit 100 already has the information related to the association between each conveying device 3 and the related tube 4 (if present), it also has the information related to which incoming conveying device 3 must be diverted or not on the secondary lane 5. This information is already communicated beforehand to the control board of the whole process station 1 and hence to the intelligent control board of antenna 6 as an actual list containing the conveying devices 3 which, once arrived close to the connection stretch 7a, must be diverted.

Such a list may also be updated dynamically according to the changing addressing needs of the conveying devices 3 typical of a laboratory automation system.

Thus, the arrival of the conveying device 31 at antenna 6 (FIG. 2) activates the suitable communication with sensors 10, 11a and 11b mounted laterally with respect to the conveyor belt 21, right close to the connection stretch 7a, and electrically connected to the antenna board.

In the practice, antenna 6 is intended to detect the ID of the incoming conveying device 31, recognize it, compare it with the list it has in the control board thereof (containing the path that each conveying device must follow) and thus alert sensors 10, 11a and 11b about the upcoming arrival of a conveying device to be diverted or not.

The location of antenna 6, which by a certain extent on the conveyor belt precedes that of sensors 10, 11a and 11b, is devised based on the intrinsic capability of antenna 6 to instantaneously read and identify the conveying device 31, due to its control board, without the need of stopping it.

On the contrary, this is not possible in known solutions: in order to make the identification, the antenna needs the conveying device to be stationary, thus it is blocked by a stopping gate, the ID thereof is detected by the communication between antenna and transponder of the conveying device and only after that, the gate retracts and the unblocked conveying device proceeds to then be diverted or not, according to the information coming from the control unit.

On the contrary, in the subject solution, using the capability of antenna 6 to read the conveying devices without stopping them, this reading is done in advance along the belt (FIG. 2) so that, once the conveying device 31 has reached the sensors (FIG. 3), the latter certainly are already ready for the arrival of a conveying device 31 to be diverted or not and thus already prepared to activate or not cam 13.

It is therefore possible to think of the stretch of belt comprised between antenna 6 and the sensors as a sort of safety margin so that, during the travel of the conveying device 31 in this stretch, the communication between the control board of antenna 6 and sensors 10, 11a and 11b certainly takes place. Accordingly, purely theoretically and according to reasonable minimum and maximum distance limits, the length of this stretch may be shortened as desired according to the extent the speed of this electrically managed communication is relied upon, in terms of performance.

The conveying device 31, once gone past antenna 6, then reaches the sensors located on the sides of belt 21. Of course, the whole series of conveying devices flows forward, i.e. in a quick succession the second conveying device 32 is read and identified by antenna 6 and so on, for each one of the other subsequent conveying devices.

Figure 3:
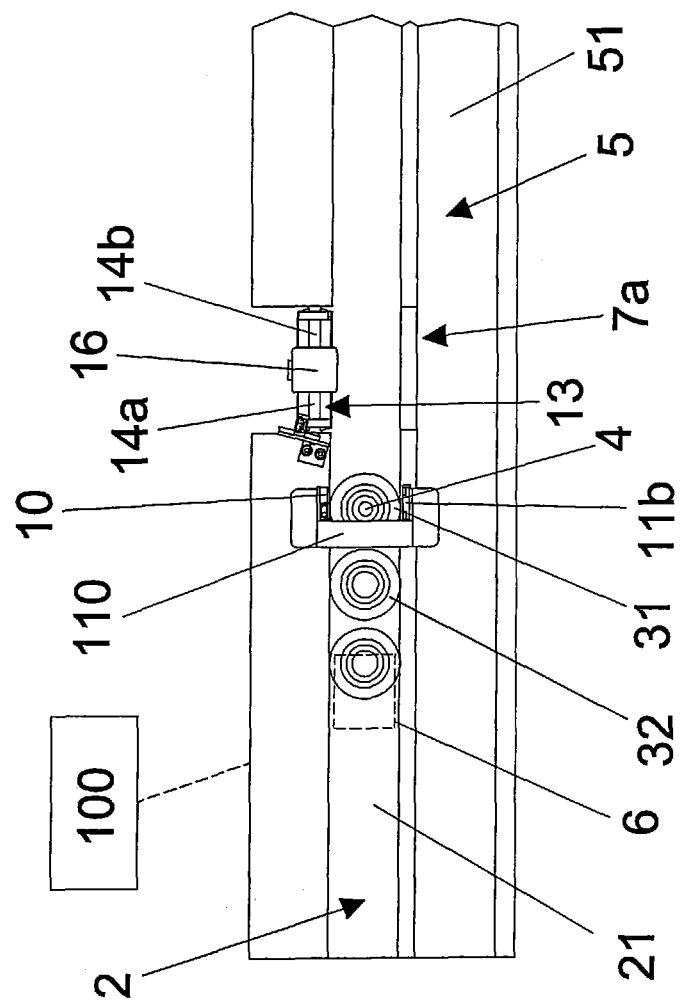

Going back to analyze the various movement steps of the first conveying device 31, it then reaches the tube detection sensor 10 and the conveying device detection sensor formed by the emitter 11a-receiver 11b pair (FIG. 3). Preferably, sensor 10 is in a position overlying emitter 11a (for this reason, in FIGS. 2-8, in a top view, emitter 11a is hidden by sensor 10); in this way, the detection of the tube, if present, carried out by sensor 10 takes place at the same time as the detection of the conveying device by the sensor formed by the pair 11a-11b, the reading window of sensor 10 being narrower than that of pair 11a-11b and thus comprised within the latter. However, the tube detection sensor 10 only serves as a confirmation sensor, adapted to detect the presence or absence of a predetermined tube in the conveying device 31 according to what expected based on the detection of the ID of the conveying device 31, carried out by antenna 6, and on the information about each conveying device-tube association (or the information of empty conveying device) already contained in the control unit 100 and previously transferred first to the control board of the whole process station 1, and hence to the control board of antenna 6.

On the contrary, the conveying device detection sensor is actually synchronized with the electrical motor 16 which actuates cam 13. In fact, irrespective of the presence or not of a tube 4, each conveying device 3 may be diverted or not according to the information previously transferred by the control unit 100, and of course four different cases may occur: i.e. diverting a conveying device with tube, diverting a conveying device without tube, not diverting a conveying device with tube, not diverting a conveying device without tube.

This depends on the addressing needs, established in advance by the control unit 100, of the single conveying device 3.

According to this, if a conveying device needs not be diverted, once read by the conveying device detection sensor formed by emitter 11a and receiver 11b, it continues straight on without the actuation of cam 13.

Figure 4:
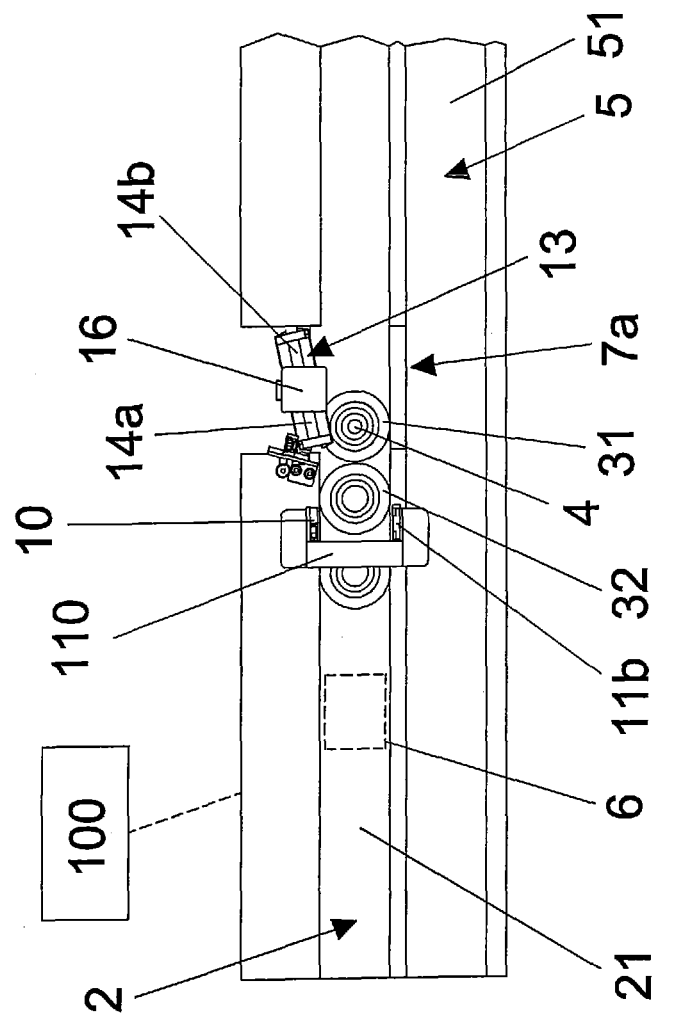

On the other hand, assuming that it is necessary to divert the conveying device 31 along the secondary lane 5, as soon as its passage is detected by the emitter-receiver pair (FIG. 3), the synchronism characterizing the diverting unit 20 and which depends on the intelligent control board of antenna 6, by means of the electrical motor 16 starts the rotation of the central shaft 15 and of cam 13 therewith, which therefore impacts the conveying device 31 (FIG. 4).

In particular, in the contact step with the conveying device 31, cam 13, by virtue of its profile which is wider in the top part and narrower in the bottom part (FIG. 10), impacts both against collar 33 and against body 34 of the conveying device 31, ensuring an even thrust to the conveying device 31 and a less sharp movement compared to known diverting systems.

Figure 15:
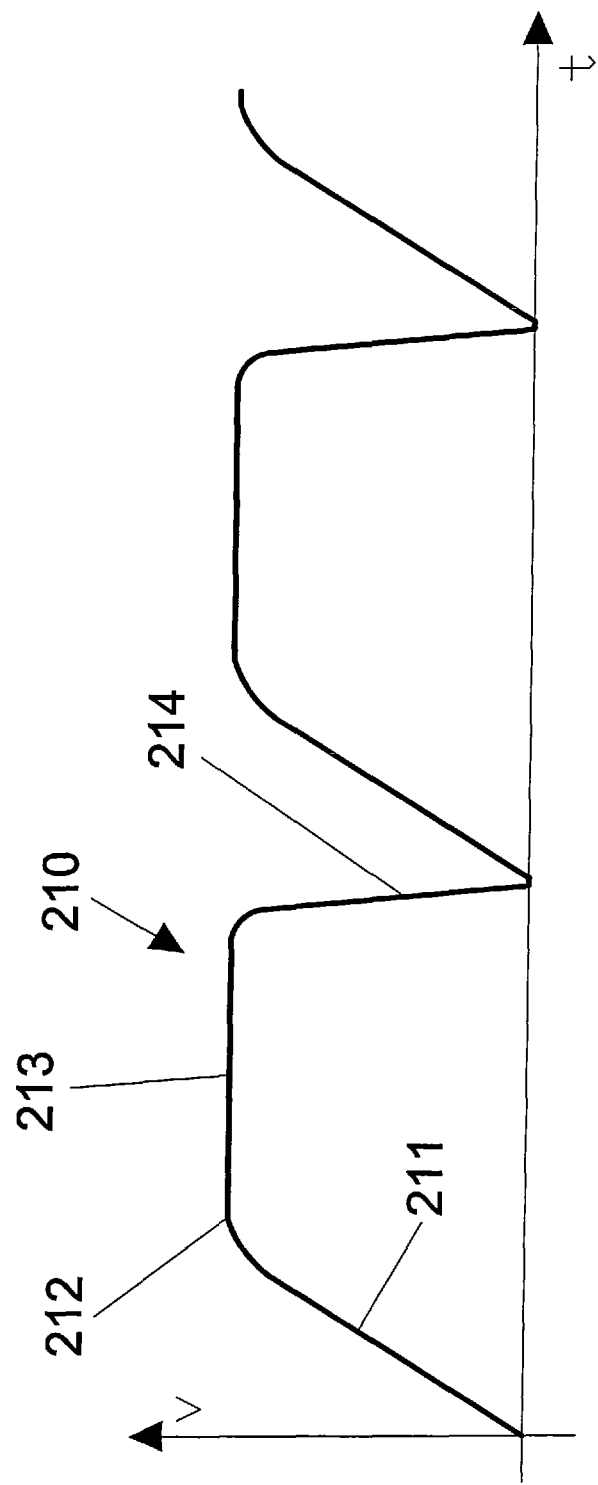
FIG. 15 shows a speed-time graph of the cam speed and thus the acceleration profile which is periodically repeated for each actuation of the same.

Moreover, the electrical motor 16 impresses a movement to cam 13 which is characterized by a particular speed profile 210, electronically managed ("electronic cam") and shown in FIG. 15. It has an initial increasing speed (and constant acceleration) step 211, corresponding to the initial step of impact of cam 13 with the conveying device 31, to then reach a maximum speed peak 212 at a moment when cam 13 has already released the conveying device 31 to divert it; hence forward, the cam continues its motion at constant speed 213 (and thus, null acceleration) to then finally undergo a deceleration (stretch 214) and return to its initial stand-by position.

Of course, due to the moving speed of cam 13 and the very short duration of the impact between the conveying device 31 and cam 13 (in the order of milliseconds), the speed variations of the cam are almost invisible to the naked eye.

Figure 5:
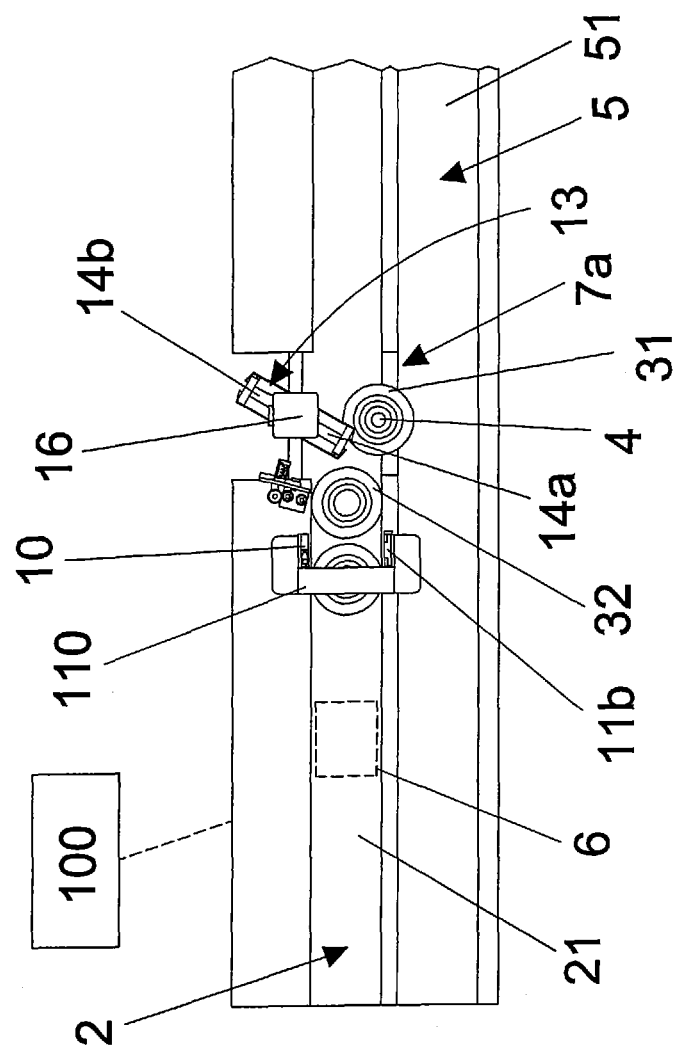
Figure 6:
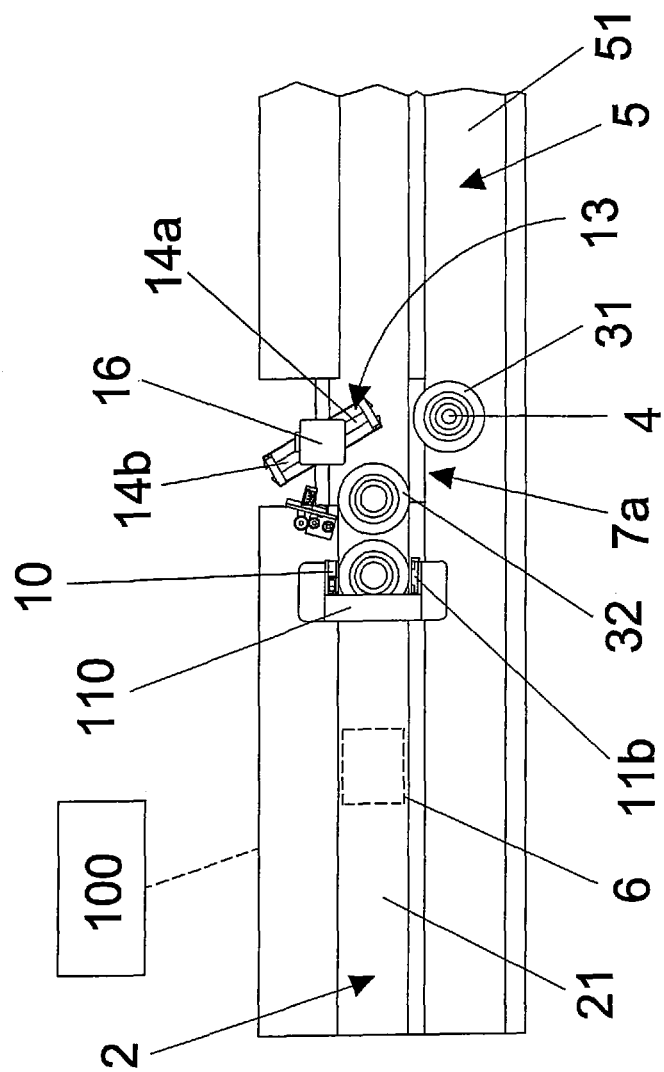
Figure 7:
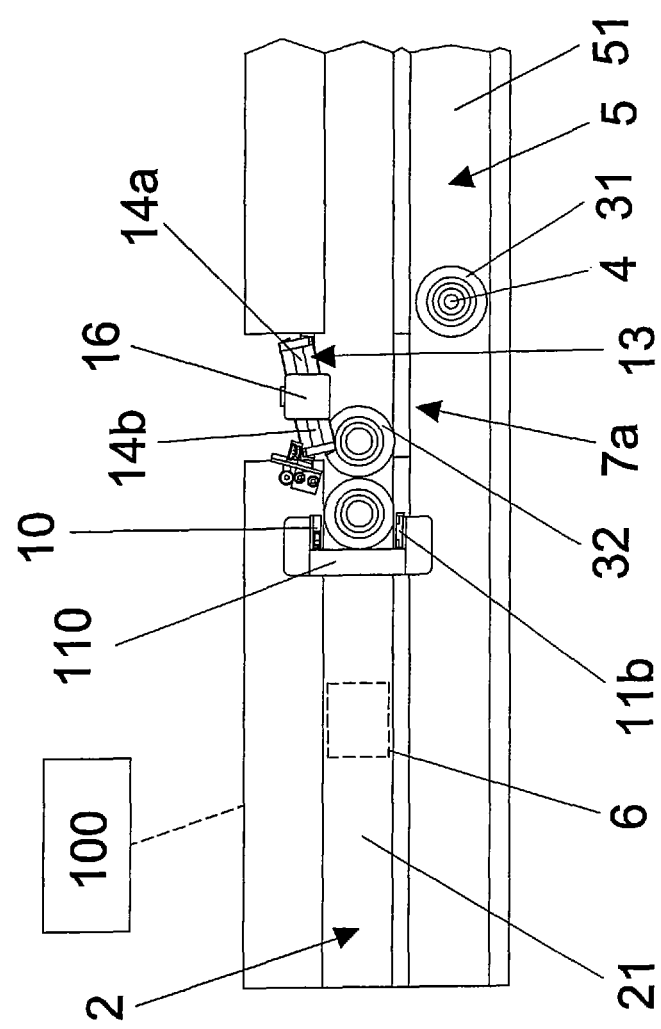

FIG. 5 shows the step in which the conveying device 31 crosses the connection stretch 7a and pushed by cam 13 that has reached its maximum speed peak 212, moves from the main lane 2 to the secondary lane 5, whereas the next FIG. 6 shows the step in which cam 13 has already released the conveying device 31, by now diverted and sent to continue its travel along the secondary lane 5, and then returns to its initial stand-by position decelerating in the final step. Meanwhile, the next conveying devices in the series follow the path along antenna 6 and sensors 10, 11a and 11b already described with reference to the conveying device 31, and when the latter has been released cam 13, once returned to the stand-by position, is already ready to interface with the next conveying device 32, and optionally to divert if necessary.

In fact, whenever the cam is actuated to divert a conveying device, it carries out a 180 degree rotation around its axis, represented by shaft 15, and this allows the management of the possible arrival of a series of conveying devices close to each other, all to be diverted (FIG. 15, periodical speed profile of the cam), since the two opposite ends 14a and 14b of cam 13 alternately exert the thrust on the conveying devices. As a consequence thereof, the next conveying device 32, which in the illustrated embodiment is assumed to be diverted too, is pushed into the secondary lane 5 by end 14b of cam 13 (FIG. 7), which with respect to the central shaft 15, is opposite end 14a that has previously diverted the conveying device 31 (FIGS. 4-6).

On the other hand, if one of the next conveying devices needs not be diverted (which solution not shown in the figures), as before, this instruction (originally coming from the control unit 100) is transferred by antenna 6 to sensors 10, 11a and 11b and by virtue of the synchronism between pair 11a-11b and the electrical motor 16 of cam 13, when such a conveying device reaches the above pair, the rotation of cam 13 is not actuated so that the conveying device can continue straight along the main lane 2.

The whole system therefore withstands a high incoming frequency of the conveying devices 3, according to the fact that they are quickly read by antenna 6 without being no longer stopped, as described above. Accordingly, the operation of the whole diverting unit 20, and in general the flow of the conveying devices 3, is greatly speeded up.

It is also evident that if at some moments the incoming frequency of the conveying devices close to the diverting unit 20 is not so high (conveying devices are no longer in sequence), the rotation movement of cam 13 in any case stops after having processed a conveying device to be diverted, and only when the conveying device detection sensor, i.e. the pair formed by emitter 11a and receiver 11b, detects the arrival of a next conveying device it starts again, of course provided that the new incoming conveying device needs to be diverted to the secondary lane 5.

In the cases described above in which the diversions of conveying devices are not consecutive, the graph of FIG. 15 obviously has a wider stretch at null speed between one profile 210 and the next one.

A procedure to implement in case of emergency is further provided, in case of various problems downstream of the diversion point or in any case in any other point of the automation system, which require the setting of a block to the flow of the conveying devices 3 at the diverting unit 20, so that the problem occurred may be solved and then the conveying devices 3 can go back to flow normally.

Such an emergency procedure is again allowed by the control board of antenna 6, which is capable of recognizing the occurrence of a problem, or in any case of an abnormal situation that requires being solved with maintenance operations on station 1 and temporarily blocking the flow of the conveying devices 3. This occurs by controlling the projection of the stopping gate 23 on the side of the main lane 2 (FIG. 8), as well as switching off motor 16 which actuates cam 13. It is clear that in this step, the synchronism between cam 13 and the conveying device detection sensor that is engaged with the first one of a possible series of temporarily blocked conveying devices 3 fails, although temporarily.

At the same time, the control board of antenna 6 alerts the control board of the process station 1 (and hence, the information is then transferred to the control unit 100) of the occurrence of an emergency situation that had required the projection of the stopping gate 23. The control unit 100 then has the task of optionally controlling the block of the conveying device flow also in other points of the automation system (for example in the process stations upstream of 1), for preventing the forming of too long queues of conveying devices at the diverting unit 20 of the process station 1.

FIG. 9 shows in more detail the two different positions taken by the stopping gate 23, which is totally similar to that described in patent EP-2225567 to the Applicant. In particular, the stand-by (or "open") position is shown on the left, where gate 23 lets the conveying device 3 flow, whereas the "closed" position taken by the stopping gate 23, after a counter clockwise rotation, for blocking the conveying device 3, is shown on the right.

Once the above abnormal situation has been solved, the control board of antenna 6 controls the return of the stopping gate 23 (by a clockwise rotation and thus the return to the "open" configuration) and the concurrent restart of motor 16 and of the synchronism between the conveying device detection sensor and cam 13, so that the conveying devices 3, now again free to flow along bell 21, may again be diverted or not according to the needs.

The conveying devices 3 optionally diverted to the secondary lane 5 therefore flow along the motorized conveyor belt 51 and, once interfaced with a predetermined (pre-testing, testing or post-testing) module, at the end of the secondary lane 5 they must return along the main lane 2. Here the return unit 30 comes into play. In known solutions, the return is managed by means of a sensor system based on which the passage of the conveying device 3 is detected, typically at the end of the secondary lane 5, and a stopping gate is actuated at this detection on the main lane 2, also in a position close to the connection stretch 7b, comprising a selector which, rotating, projects from the side wall of the main lane 2 and blocks any conveying devices 3 flowing by, allowing the return of the conveying devices 3 from the secondary lane 5.

On the contrary, the solution proposed in the present patent consists in eliminating any kind of sensor system and stopping gates for managing the return of conveying devices 3.

In fact, a conveying device 35 (FIG. 11) arrived at the end of the secondary lane 5 reaches the connection stretch 7b; here, the side surface 350 of the conveying device 35 meets belt 9, actuated as said by the system controlled by the electrical motor 19 and comprising shaft 22 and pinions 8a and 8b (FIG. 13).

Of course, the rotation of belt 9 follows the direction of the desired return movement of the conveying device 35 (in the present embodiment, the direction is clockwise), and the conveying device 35 is thus pulled by simple friction along the connection stretch 7b: substantially, the thrust of the horizontally-placed conveyor belt 51 of the secondary lane 5 underlying the conveying device 31 is added to the thrust of belt 9, having a vertically-placed surface 91 and which interacts with the side surface 350 of the conveying device 35. In this way, the conveying device 35 starts rotating during this dragging (FIG. 11), then entering (FIG. 12) the main lane 2 between two consecutive conveying devices 36 and 37 which travel, optionally close to each other, along the main lane 2 itself. This happens because the side surface 350 of the conveying device 35 in counter clockwise direction rests on the side surfaces 360, 370 of the conveying devices 36 and 37 and pivoting on both, it lets the conveying device 36 flow away, while substantially blocking the conveying device 37 and entering in front of it in the main lane 2. The conveying device 35 rotates in counter clockwise direction around its vertical axis of symmetry due to the clockwise movement of belt 9, and upon contact it causes the rotation in the opposite direction of device 36 and above all, of device 37 which actually flows on the underlying conveyor belt 21 rotating in clockwise direction (opposite the direction of rotation of device 35) without translating, but rather being moved by the device 35 itself slightly backwards. The interaction of the conveying device 35 causes a slight clockwise rotation and above all, a further forward thrust, on device 36. Accordingly, a gap between devices 36 and 37 is created for inserting device 35 and any risk of jamming between the returning device 35 and devices 36 and 37 traveling along the main lane 2 is prevented.

It should be noted that if for a certain time the pre-testing, testing or post-testing module present along the secondary lane 5 does not release any previously diverted conveying device, and thus there is no need to return any of them along the main lane 2, the electrical motor 19 that controls the rotation of belt 9 may be temporarily switched off for energy saving reasons, and the belt would of course be temporarily blocked.

When the module releases a conveying device again, at the same time the electrical motor 19 is restarted and the rotation of belt 9 is resumed.

Figure 14:
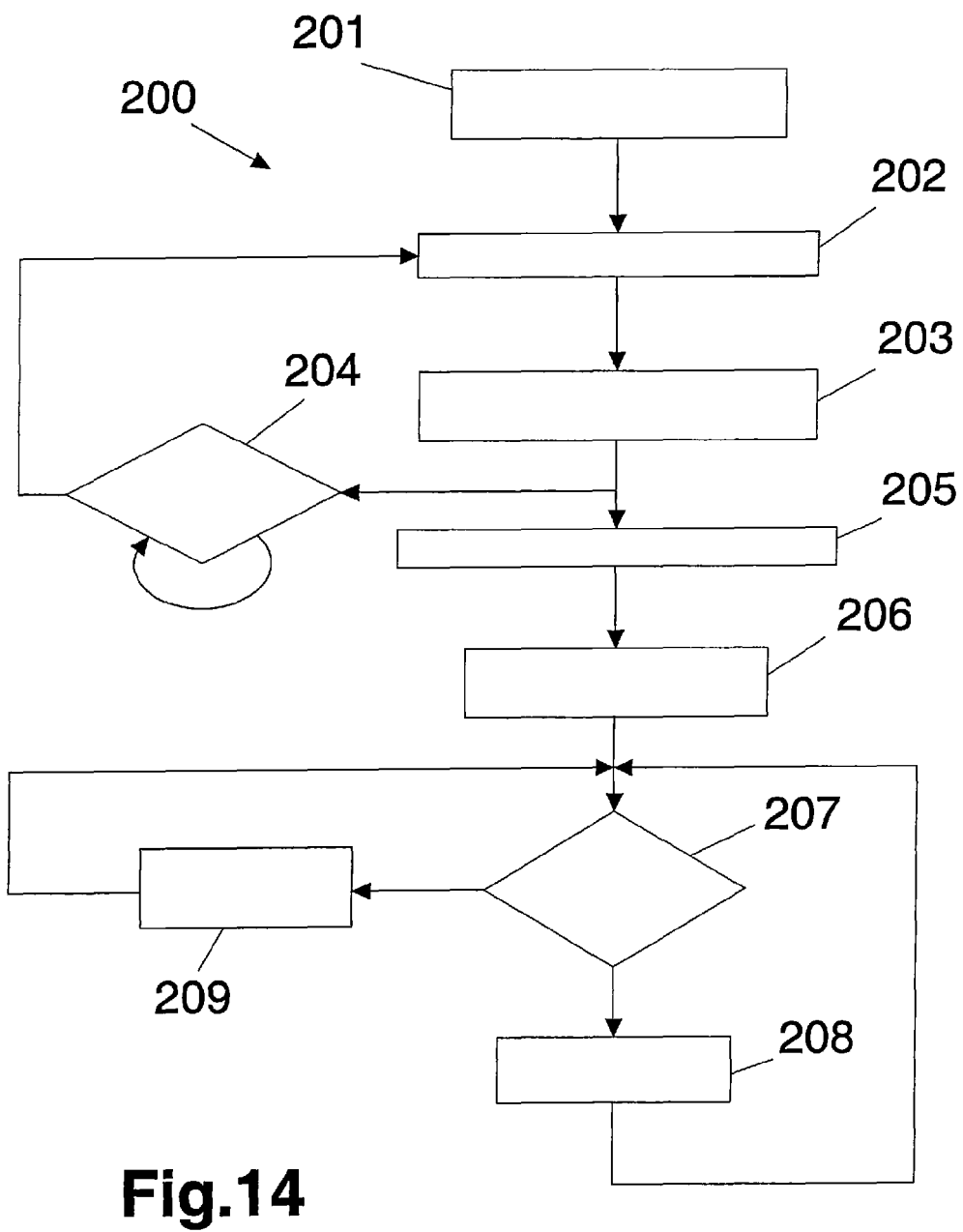
FIG. 14 shows a block diagram that explains the various steps of the method related to the operation of the diverting unit.

A method 200 related to the subsequent operative steps of only the diverting unit 20 of the process station 1, in the absence of problems or abnormal and unexpected situations, is described in FIG. 14.

In the first place, step 201 refers to the communication, by the control unit 100 to the control board of antenna 6, through the control board of the process station 1, of a list containing the list of conveying devices, among those that interface with the process station 1, that need to be diverted.

Thereafter, at step 202, the ID of the first conveying device 31 arriving at antenna 6 is read by the antenna itself and, based on the fact that such a conveying device belongs or not to the above list, the information as to whether the subject conveying device 31 must be diverted or not is stored by the control board of antenna 6 (step 203) based on the future actuation of the synchronism between the conveying device detection sensor and the diverting device (cam) 13.

The cycle is repeated for any close-by arrival, at antenna 6, of any subsequent conveying device (step 204) thus returning, for any of them, to the previous identification and information storage steps.

When the conveying device 31 reaches the sensor consisting of the emitter 11a-receiver 11b pair (step 205), the synchronism between the sensor itself and cam 13 is instantaneously activated (step 206). This means that based on the previously stored information, i.e. whether the conveying device 31 must be diverted or not (step 207), the next step may be the rotation of cam 13 (step 208) so that the conveying device 31 may be diverted from the main lane 2 to the secondary lane 5, or the non-actuation of cam 13 (step 209) if the conveying device must continue straight along the main lane 2. The process is therefore repeated in a cascade for all the conveying devices that interface with the process station 1 in the point before the diversion, irrespective of the incoming frequency thereof. The innovative aspect of the finding is therefore given by the fact that, while being structurally very different, both the diverting unit 20 and the return one 30 carry out the function of allowing a continuous flow of conveying devices 3 into the process station 1, eliminating the typical need of known systems of having to stop these conveying devices at each diversion point from the main lane 2 or return to the main lane.

As regards the diverting unit 20, this is obtained due to the provision, close to an optional diverting point, of a synchronization mechanism between the control board of the antenna, the sensor that detects the presence of conveying devices 3 flowing along the main lane 2 and the diverting device 13 which optionally diverts the conveying devices 3; such a synchronization mechanism is devised so that none of the incoming conveying devices must be stopped, even if they arrive at the diverting point one after the other in a quick succession.

As said, this aspect is related to the presence, upstream of the diverting point, of an antenna 6 which is capable of reading the incoming conveying devices 3 and identify them without stopping them. In particular, the control board of the antenna that allows this immediate reading represents a considerable step forward compared to known systems, in which it is always necessary to block the conveying device 3 to allow the reading thereof by antenna 6 and therefore provide, at the same antenna located before the diversion, for a stopping gate that projects from the side wall of the conveyor to carry out this blocking function.

In the practice, while in known systems antenna 6 is substantially part of the control board of the whole process station, on the contrary in the solution of the present patent it is provided with its own intelligent control board which, being suitably synchronized, through the control board of station 1, with the control unit 100 as well as with the tube detection sensors 10, 11*a* and 11*b* and conveying devices, allows all the diverting process of the conveying devices 3 along the process station 1 to be managed.

In any case, a stopping gate is provided at the diverting unit 20 but its function now is only that of blocking the conveying devices in particular emergency situations; therefore, it does not come into play in the normal operation of the diverting unit itself as it happens in known solutions.

Another innovative aspect is that of placing such an antenna 6, underneath the conveyor belt 21 of the main lane 2, in advance by a certain stretch with respect to sensors 10, 11*a* and 11*b*, i.e. at the point immediately before the diversion, while in known systems antenna 6 is located at the tube detection sensor (the only one provided) and thus at the point immediately before the diversion, so that at the same time the ID of the conveying device 3 is detected by antenna 6 and tube 4 (if provided) is detected by sensor, but all with stationary conveying device 3 and thus with considerable slowing down.

Moreover, the adoption of a cam like that described above as diverting device 13 ensures a more even thrust on the conveying device 3 accompanying it in a smoother manner as compared to the known diverting devices.

Above all, the provision of a motor capable of electrically managing the cam speed profile represents a highly innovative concept compared to a known system where the increasing thrust impressed by the cam to the conveying device is only the result of a particular geometrical shape of the cam itself (for example, a helical shape to impart a stronger thrust in the thinner end portion thereof).

Moreover, by rotating by 180 degrees at a time, cam 13 is capable of better withstanding a high flowing frequency of conveying devices 3 to be diverted one after the other, as compared to known diverting devices mostly based on a lever which is pneumatically actuated and which therefore, having to open and close continuously, often is not capable of withstanding a possible flow of conveying devices 3 close to each other and all to be diverted.

In the practice, it has been seen that the system thus described can achieve the objects set ensuring a speeding up of the identification and optional diversion process of the conveying devices 3 from a main 2 to a secondary lane 5 within a process station 1 of an automatic conveyor of a laboratory automation system, preventing blocks to the conveying device flow in this step. Moreover, likewise, blocks in the flow are also prevented in the subsequent return step of the previously diverted conveying devices 3, which return into the main lane 2 without any risk of jamming with those that have continued their travel along the main lane 2 as they have not been diverted.

This is especially valid, in both steps, in situations where the frequency of conveying devices that interface with the diverting and/or return unit is particularly high.

If referred to the plurality of process stations 1 in a series that form the automatic conveyor as a whole, this leads to an overall speeding up in the flow of conveying devices 3 along the whole automation system.

Several changes and variations may be made to the invention thus conceived, all falling within the scope of the inventive concept.

In the practice, the materials used as well as shapes and sizes, may be any, according to the requirements.

The invention claimed is:

1. A process station of conveying devices for conveying biological product containers comprising a main lane for the flow of said conveying devices and a secondary lane for the flow of said conveying devices connected to each other by connection stretches, comprising a diverting unit for said conveying devices from said main lane to said secondary lane and a return unit for said conveying devices from said secondary lane to said main lane, wherein each of said diverting units and each of said return units are provided with means adapted to allow the identification, control and detection of said conveying devices without interrupting the motion thereof, in advance with respect to the actuation of diverting means for the same from one lane to the other, said diverting unit comprising a diverting device comprising a cam provided with two side portions rotating around a central shaft, each of said two side portions being adapted to impact one of said conveying devices, said return unit comprising a motorized belt adapted to interact with an outer side cylindrical surface of the conveying device so as to set said conveying device in rotation around a vertical axis without interrupting the motion of said conveying devices the flow of which is therefore continuous.

2. The process station according to claim 1, wherein said diverting unit comprises, located upstream of said connection stretch and along the main lane, first identification and control means of said conveying devices, then detection means of said conveying devices during the motion of said conveying devices in said main lane, said means being connected to a control unit adapted to control a diverting device of said conveying devices located downstream of said means by such a space to allow the diversion of said selected conveying devices without the stop thereof in said main lane.

3. The process station according to claim 1, wherein said two side portions being rotating around a central shaft of an electrical motor, and being provided with a shaped profile that allows each of said side portions to impact one of said conveying device at time.

4. The process station according to claim 3, wherein the cam rotates at a variable speed.

5. The process station according to claim 1, wherein said return unit comprises, at the return connection stretch of the conveying device, said motorized belt.

6. The process station according to claim 5, wherein said motorized belt is vertically positioned stretched between two pinions with vertical axis of rotation, and is provided with a vertical flat contact surface adapted to interact with said outer side cylindrical surface of the returning conveying device so as to set it in rotation to facilitate the return in the presence of a conveying device in motion in the main lane.

7. A method for diverting conveying devices of biological product containers between a main lane and a secondary lane of a process station, wherein the method provides for the identification, control and detection of said conveying devices without interrupting the motion thereof, in advance with respect to the diversion thereof from one lane to the other still without interrupting the motion of said conveying devices the flow thereof is therefore continuous, for the diversion of conveying devices of biological product containers from a main lane to a secondary lane of a process station, the method comprises the following steps in a time sequence:

communication by a control unit to a control board of identification and control means of a list containing the list of conveying devices to be diverted, said list being dynamically updated;

identification of each of said incoming conveying devices by said identification and control means;

storage by said control board of said identification and control means of the information related to the need of diverting or not each of said incoming conveying devices;

actuation of detection means of said conveying devices;

actuation of a diverting device if the conveying device that has reached said detection means of said conveying devices must be diverted from said main lane to said secondary lane, or block of said diverting device if said conveying device must continue without being diverted.

8. The method according to claim 7, wherein for the return of a conveying device of biological product containers from a secondary lane to a main lane of a process station, the method provides for the automatic actuation for the rotation of the returning conveying device around a vertical axis at a return connection stretch from said secondary lane in said main lane wherein further conveying devices flow.

\* \* \* \* \*